(12) United States Patent
Pepera

(10) Patent No.: US 6,793,636 B1
(45) Date of Patent: *Sep. 21, 2004

(54) THERAPEUTIC DEVICE FOR TREATING FOOT PATHOLOGIES

(76) Inventor: Jane M. Pepera, 4651 Jaycox Rd., Avon, OH (US) 44011

( * ) Notice: Subject to any disclaimer, the term of this patent is extended or adjusted under 35 U.S.C. 154(b) by 0 days.

This patent is subject to a terminal disclaimer.

(21) Appl. No.: 10/315,600

(22) Filed: Dec. 10, 2002

Related U.S. Application Data

(63) Continuation of application No. 09/771,736, filed on Jan. 29, 2001, now Pat. No. 6,499,485.

(51) Int. Cl.[7] ............................................. A61H 15/02
(52) U.S. Cl. ...................... 601/15; 601/121; D24/211; D24/207
(58) Field of Search ............................. 601/15, 19, 22, 601/27, 28, 32, 120, 121, 118, 122, 125, 126; D24/211, 212, 213, 208

(56) References Cited

U.S. PATENT DOCUMENTS

| | | | |
|---|---|---|---|
| 896,484 A | * 8/1908 | Thoms | 601/120 |
| 1,229,658 A | 6/1917 | Sandow | |
| 1,722,866 A | * 7/1929 | Snyder | 601/121 |
| 2,448,797 A | * 9/1948 | Gustin | 601/19 |
| 2,546,095 A | 9/1951 | Gustlin | |
| 3,842,453 A | * 10/1974 | Redfield | 601/121 |
| 3,888,241 A | 6/1975 | Fischer | |
| D243,557 S | 3/1977 | Kientz | |
| 4,109,649 A | 8/1978 | Iyomasa | |
| D253,373 S | 11/1979 | Celeste | |
| D256,503 S | 8/1980 | Moustakas | |
| 4,378,007 A | * 3/1983 | Kachadourian | 601/121 |
| 4,756,311 A | 7/1988 | Francis, Jr. | |
| 4,920,964 A | 5/1990 | Francis, Jr. | |
| 5,411,470 A | * 5/1995 | Liptak et al. | 601/118 |
| 5,577,995 A | * 11/1996 | Walker et al. | 601/120 |
| 5,685,828 A | 11/1997 | Dyck | |
| 5,798,411 A | 8/1998 | Riazi | |
| 5,824,013 A | 10/1998 | Allen | |
| 6,129,687 A | 10/2000 | Powell et al. | |

* cited by examiner

Primary Examiner—Danton D. DeMille
(74) Attorney, Agent, or Firm—Fay, Sharpe, Fagan, Minnich & McKee, LLP

(57) ABSTRACT

A theraputic device for treating foot pathologies. The device includes a generally-cylindrical body having a first end section, a spherical center section, a first intermediate section extending axially between the first end section and the center section, a second end section, and a second intermediate section extending axially between the second end section and the center section. The center section defines a convex working surface. The first intermediate section cooperates with the first end section and the center section to define a first concave working surface. The second intermediate section cooperates with the second end section and the center section to define a second concave working surface. The device can be filled with a gel adapted for exposure to heat and cold.

1 Claim, 2 Drawing Sheets

THERAPEUTIC DEVICE FOR TREATING FOOT PATHOLOGIES This application is a continuation of U.S. application Ser. No. 09/771,736 filed Jan. 29, 2001, now U.S. Pat. No. 6,499,485.

BACKGROUND OF THE INVENTION

The present invention relates to the therapeutic device art. The preferred embodiment of the invention finds particular application in conjunction with a therapeutic device for treating various foot pathologies such as plantar fasciitis, heel spurs, etc., and will be described with particular reference thereto.

The plantar fascia is a tough fibrous band of connective tissue beginning at the calcaneus (the heel of the foot) extending to the metatarsal heads (the ball of the foot). It supports the arch and with each step the plantar fascia unloads the force of the foot and distributes it accordingly. Plantar fasciitis is an inflammation of the plantar fascia. This condition can occur independently or in conjunction with heel spurs. Either situation results in pain along the bottom of the foot.

Options for treating plantar fasciitis include performing stretching exercises, wearing night splints, wearing orthotics, receiving ultrasound treatments in conjunction with stretching exercises, receiving cortisone injections, and surgery. In physical therapy, the treatment includes a combination of that listed above. The intention is to stretch the plantar fascia, by using heating modalities prior to the stretch. Currently the method for heating the plantar fascia is ultrasound, an expensive modality in a rehabilitation facility. The second objective is to combine heat and a stretching exercise so that the plantar fascia can be stretched when in a more elastic state (as in heating).

No method exists that fulfills this heating and stretching objective. There is a method currently utilized to stretch the plantar fascia by performing a can roll. This is where the patient is taught to use a common household item such as a can of hair spray or a soup can to roll their foot back and forth.

Accordingly, it is considered desirable to provide a new and improved therapeutic device for treating various foot pathologies that meets the above-stated needs and overcomes the foregoing difficulties and others while providing better and more advantageous results.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE PREFERRED EMBODIMENTS

Figure 1:
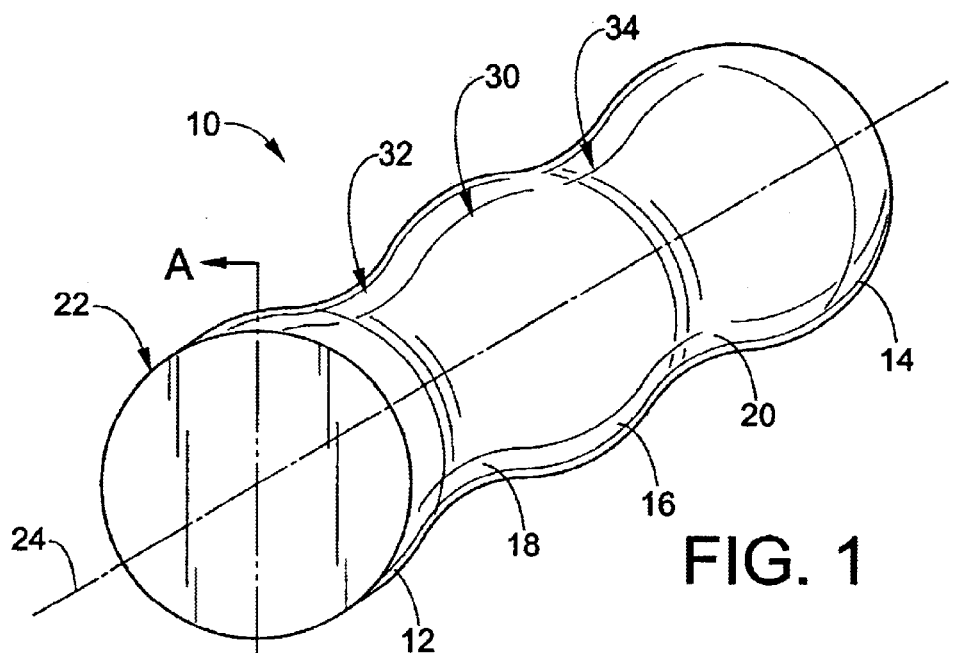
FIG. 1 is a perspective view of a therapeutic device in accordance with a first embodiment of the present invention.
Figure 2:
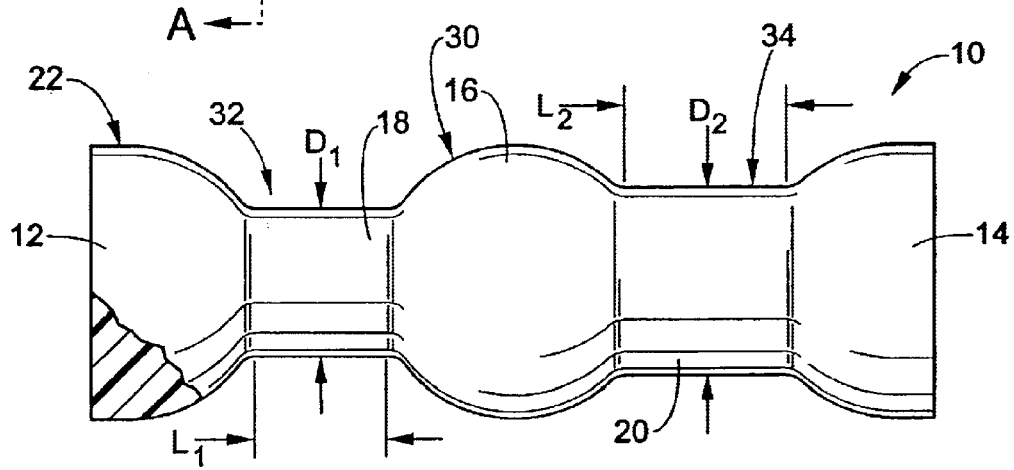
FIG. 2 is a side elevation view, partially broken away, of the therapeutic device of FIG. 1.

With reference now to FIGS. 1 and 2, a therapeutic device 10 is molded, formed, shaped, configured, or otherwise fashioned into a solid, generally-cylindrical body or configuration having a first end section 12, a second end section 14, a center section 16, a first intermediate section 18, and a second intermediate section 20. The first and second end sections 12, 14, center section 16, and intermediate sections 18, 20 cooperate to define an undulating, generally cylindrical, outer surface 22 that extends axially along a central longitudinal axis 24 of the device 10, and that is shaped to isolate and to facilitate the stretching of the plantar fascia.

The first and second end sections 12, 14 have generally-cylindrical shapes. The center section 16 has a generally-spherical shape. The first intermediate section 18 has a generally-hourglass shape that extends axially along the central longitudinal axis 24 between the first end section 12 and the center section 16. In addition, the first intermediate section 18 has a throated portion with a diameter of about $D_1$ and a length of about $L_1$.

Likewise, the second intermediate section 20 has a generally-hourglass shape that extends axially along the central longitudinal axis 24 between the center section 16 and the second end section 14. The second intermediate section 20 has a throated portion with a diameter of about $D_2$ and a length of about $L_2$. In the embodiment being described, the length $L_1$ is about equal to or less than the length $L_2$, and the diameter $D_1$ is about equal to or less than the diameter $D_2$.

The center section 16 defines a generally-convex working surface 30 for working a central longitudinal region of the plantar fascia. The first intermediate section 18 cooperates with the opposing sloped portions of the first end section 12 and the center section 16 to define a first generally-concave working surface 32 for working intermediate longitudinal regions of the plantar fascia extending along each side of the central region thereof. That is, the opposing sloped surfaces of the first end section 18 and the center section 22, respectively, are spaced apart a predetermined distance $L_1$ to contact the intermediate longitudinal regions of the plantar fascia outward of the central region.

Likewise, the second intermediate section 20 cooperates with the opposing portions of the second end section 14 and the center section 16 to define a second generally-concave working surface 34 that is shaped different from the first generally-concave working surface 32. The second generally-concave working surface 34 is shaped to work the longitudinal side edges of the plantar fascia outward of the intermediate regions thereof. That is, the opposing sloped surfaces of the second end section 14 and the center section 16, respectively, are spaced apart a predetermined distance $L_2$ to contact the side edges of the plantar fascia outward from the intermediate regions of the plantar fascia.

The therapeutic device 10 can be formed from any known or otherwise conventional compressible, resilient or elastic, natural or synthetic, composition or compositions such as rubber, elastomers, etc. In the embodiment being described, the therapeutic device 10 is formed from a compressible, resilient, polyurethane composition. A compressible polyurethane composition suitable for use with the therapeutic device 10 is disclosed in U.S. Pat. No. 5,798,411, which disclosure is hereby incorporated by reference. Briefly, as disclosed in the '411 patent, the compressible polyurethane composition includes 140 parts by weight of a diol; from about 50 to 70 parts by weight of a diisocyanate compound, the diols and diisocyanate compounds being selected from the group consisting of reactants capable of forming polyurethanes; from about one to 30 percent by weight of a plasticizer, based upon the weight of the polyurethane composition; and from 0 to about 100 parts by weight of a mineral filler, based upon 100 parts by weight of the polyurethane composition.

In operation, the therapeutic device 10 is rolled along a substantially planar surface, e.g. the floor, with a back and forth motion by i) placing the foot, and more particularly, the arch of the foot, on the desired working surface 30, 32, or 34, and then ii) applying a gentle to medium downward force (from either a sitting or standing position) against the particular working surface 30, 32, 34 to effect a back and forth rolling motion of the therapeutic device 10 from the calcaneus to the metatarsal heads. Accordingly, the therapeutic device 10 can be used to loosen and stretch any one or more of the central, intermediate, and side regions of plantar fascia.

Figure 3:
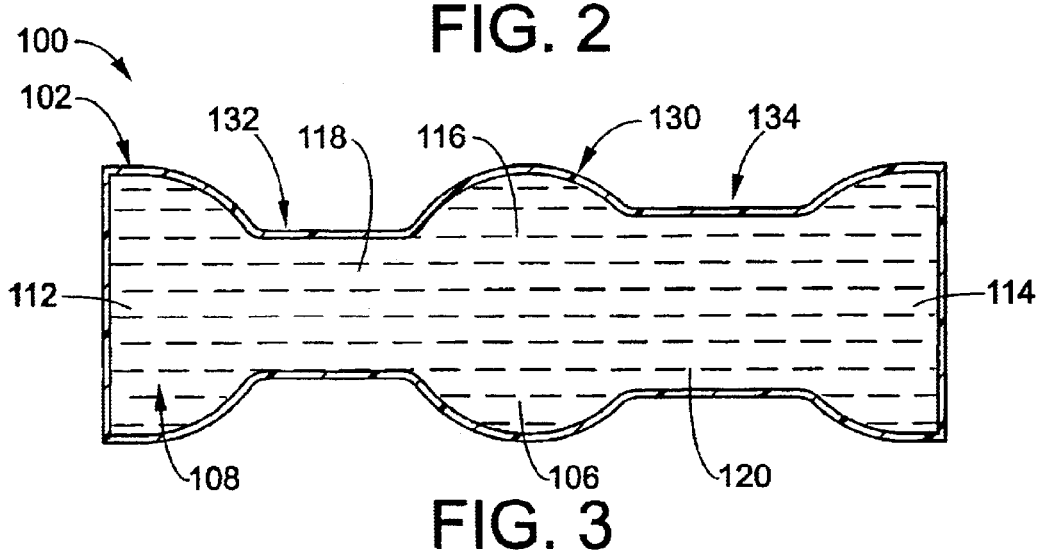
FIG. 3 is a central section view of a therapeutic device in accordance with a second embodiment of the present invention taken along the line A—A of FIG. 1.

With reference now to FIG. 3, the therapeutic device 100 includes more or more layers of polymeric sheets, films, laminates, etc. that define an outer jacket, cover, side wall, or sheathing 102 for retaining a liquid, paste, or gel material 106 that is sealed within a closed cavity 108 defined by the outer layer(s) 102. The sheathing 102 is molded, formed, shaped, or otherwise fashioned into the configuration as the therapeutic device of FIGS. 1 and 2. That is, the therapeutic device 100 includes a first end section 112, a second end section 114, a center section 116, a first intermediate section 118, and a second intermediate section 120. The first and second end sections 112, 114, center section 116, and intermediate sections 118, 120 cooperate to define an undulating, generally cylindrical, outer surface that extends axially along a central longitudinal axis of the device 100.

The first and second end sections 112, 114 have generally-cylindrical shapes. The center section 116 has a generally-spherical shape. The first intermediate section 118 has a generally-hourglass shape that extends axially along the central longitudinal axis between the first end section 112 and the center section 116. In addition, the first intermediate section 118 has a throated portion with a diameter of about $D_1$ and a length of about $L_1$ (FIG. 2).

Likewise, the second intermediate section 120 has a generally-hourglass shape that extends axially along the central longitudinal axis between the center section 116 and the second end section 114. The second intermediate section 120 has a throated portion with a diameter of about $D_2$ and a length of about $L_2$ (FIG. 2). In the embodiment being described, the length $L_1$ is about equal to or less than the length $L_2$, and the diameter $D_1$ is about equal to or less than the diameter $D_2$.

The center section 116 defines a generally-convex working surface 130 for working a central longitudinal region of the plantar fascia. The first intermediate section 118 cooperates with the opposing sloped portions of the first end section 112 and the center section 116 to define a first generally-concave working surface 132 for working intermediate longitudinal regions of the plantar fascia extending along each side of the central region thereof. That is, the opposing sloped surfaces of the first end section 118 and the center section 122, respectively, are spaced apart a predetermined distance $L_1$ to contact the intermediate longitudinal regions of the plantar fascia outward of the central region.

Likewise, the second intermediate section 120 cooperates with the opposing portions of the second end section 114 and the center section 116 to define a second generally-concave working surface 134 that is shaped different from the first generally-concave working surface 132. The second generally-concave working surface 134 is shaped to work the longitudinal side edges of the plantar fascia outward of the intermediate regions thereof. That is, the opposing sloped surfaces of the second end section 114 and the center section 116, respectively, are spaced apart a predetermined distance $L_2$ to contact the side edges of the plantar fascia outward from the intermediate regions of the plantar fascia.

The liquid, paste, or gel 106 has a low freezing point and a high boiling point. Thus, the therapeutic device 100 can be temporarily placed in hot (e.g. boiling) water, or exposed to microwave energy (such as in a microwave oven), to heat the liquid, paste, or gel 106 to a temperature that is known to provide therapeutic benefits. Likewise, the therapeutic device 100 can be temporarily placed in cold (e.g. ice) water, or placed in a freezer to cool or freeze the liquid, paste, or gel 106 to a temperature that is known to provide therapeutic benefits.

By applying heat, the plantar fascia benefits from the warmth of the modality (making the plantar fascia more elastic) in conjunction with stretching that is effected by the therapeutic device 100. By applying cold, an inflamed plantar fascia can be "iced down" in a lengthened position (as it is being stretched). Both applications of heat and cold aid in the treatment of plantar fasciitis, thus eliminating the need for time-consuming, costly, and painful procedures that this condition could incur.

A liquid, paste, or gel that is suitable for use in the present invention is disclosed in U.S. Pat. Nos. 4,756,311 and 4,920,964, the disclosures of which are hereby incorporated by reference. As disclosed in the incorporated patents, the gel is preferably formulated from: 1350 gms. Carbopol™, 0.7%; 13.5 gal. propyleneglycol, 27%; 180 gms. color dye, 0.09%; 1400 gms. formaldehyde, 0.2%; 2000 gms. sodium hydroxide, 1.0%; and 37.5 gal. water, 71.7%. Another suitable get composition is disclosed in U.S. Pat. No. 4,462,224, which disclosure is also incorporated herein by reference.

It is contemplated that the outer side wall 102 can be formed from any conventional polymeric material or materials (e.g. plastic) that have at least one or more of the following i) exhibit good thermal (e.g. heat and cold) transfer properties, ii) are able to withstand heating, such as by microwave energy, boiling water, etc. and cooling (e.g. freezing), and iii) exhibit at least limited flexible properties while maintaining the structural integrity of the therapeutic device 100, to withstand the pressures applied by the foot during use of the therapeutic device 100. It is contemplated that a conventional injection-molded plastic material, or a conventional blow-molded plastic material such as that is used to make soda pop bottles, e.g. 2-liter pop bottles, may be suitable for use as the outer side wall 102. In operation, the heated or cooled therapeutic device 100 is rolled along a substantially planar surface, e.g. the floor, with a back and forth motion by i) placing the foot, and more particularly, the arch of the foot, on the desired working surface 130, 132, or 134, and then ii) applying a gentle to medium downward force (from either a sitting or standing position) against the particular working surface 130, 132, 134 to effect a back and forth rolling motion of the therapeutic device 100. Accordingly, the therapeutic device 100 can be used to loosen and stretch any one or more of the central, intermediate, and side regions of plantar fascia. In addition, the cooled therapeutic device 100 can be used to reduce inflammation while stretching the plantar fascia, and the heated therapeutic device 100 can be used to loosen while stretching the plantar fascia.

Figure 4:
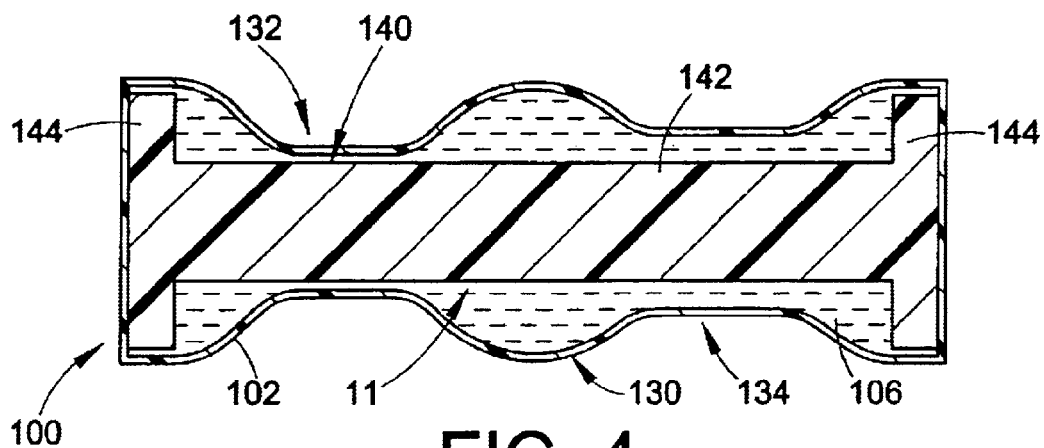
FIG. 4 is a central section view of a therapeutic device in accordance with a third embodiment of the present invention.
Figure 5:
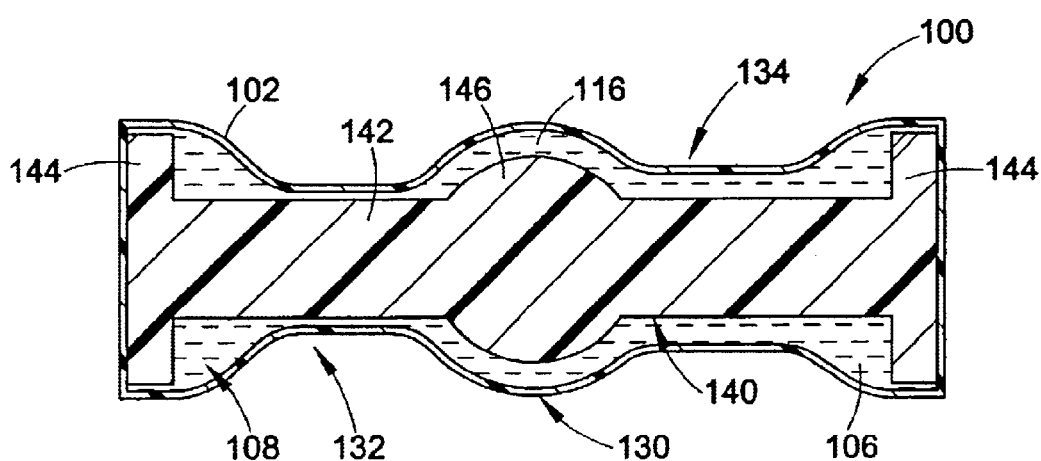
FIG. 5 is a central section view of a therapeutic device in accordance with a fourth embodiment of the present invention.
Figure 6:
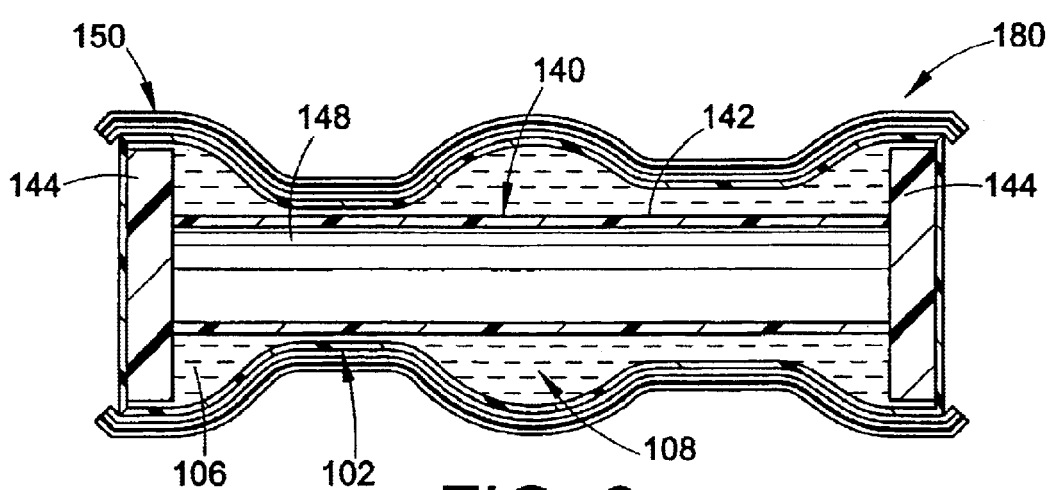
FIG. 6 is a central section view of a therapeutic device in accordance with a fifth embodiment of the present invention.

Referring now to FIGS. 4–6, it is contemplated that the therapeutic device 100 can be provided with a substantially rigid spool 140 positioned within the internal cavity 108 and at least substantially surrounded by the liquid, paste, or gel 106. The spool 140 includes a longitudinally extending cylindrical section 142 and disk-shaped end portions 144 extending generally transverse to the longitudinal axis 24 from each end of the cylindrical section 142.

The spool 140 provides additional structural integrity to the therapeutic device 100. In addition, the spool 140 provides additional resistance to the downward pressure exerted by a foot during use of the therapeutic device 100. It is contemplated that the spool 140 can more closely follow the contours of the sheathing 102 by including a spherical center section 146 (FIG. 5) that conforms with the spherical center section 116. In addition, the spool cylindrical portion 142 can be solid (FIG. 4), or can define a hollow cavity 148 (FIG. 6). The hollow cavity 148 can be sealed (as shown), or can be open to house additional liquid, paste, or gel 106.

The spool 140 can be formed from any conventional polymeric material. It is contemplated that the spool 140 could also exhibit good thermal transfer properties so as to augment the liquid, paste, or gel 106 in supplying heat or cold to the plantar fascia during use of the therapeutic device 100.

With continued reference to FIG. 6, the therapeutic device 100 can be provided with a removable or permanently-affixed outer moisture absorption and retention layer or sleeve 150 that somewhat tightly surrounds or encompasses the sheathing 102. In the embodiment being described, the sleeve 150 is formed from a cloth material such as terry cloth with elastic webbing sewn thereto. When moistened, the sleeve 150 enhances the benefits of heat and cold transfer by applying moist heat transfer or moist cold transfer to the plantar fascia.

In sum, device 10, 100 is a reusable therapeutic device for stretching the plantar surface of the foot including the plantar fascia while incorporating heat and cold modalities. Furthermore a moisture layer can be utilized to encompass moist-heat and moist-cold for added benefits of this modality. A back and forth working motion along the bottom of the foot combines stretching with the hot/cold modalities to aid in the treatment of common foot disorders. In addition, the therapeutic device 10, 100 permits patients suffering from common foot pathologies such as plantar fasciitis, the ability to treat the plantar fascia at home. Moreover, the therapeutic device 10, 100 can simultaneously apply heat while stretching the plantar fascia, and can simultaneously apply cold to reduce inflammation while stretching the plantar fascia. Lastly, the therapeutic device 10, 100 can reduce or eliminate the need for costly and time-consuming physical therapy and or medical procedures by permitting patients to successfully treat plantar fasciitis at home.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claim or the equivalents thereof.

For instance, while it has been suggested that the present invention can be used at home to treat common foot pathologies, it is clearly contemplated that such a therapeutic device could also be used in a clinical or physical therapy setting.

Further, while the present invention has been described for use with foot pathologies such as plantar fasciitis, it is recognized that the therapeutic device 10, 100 can also be used to treat medical conditions other than plantar fasciitis. For instance, it is known that heal spurs can be caused by, or can cause, plantar faciitis. Thus, the therapeutic device 100 can be cooled and then any one or more of the convex and/or concave working surfaces thereof can be used to apply pressure to the heal to relieve inflammation caused by such heal spurs. Additionally, the device 10, 100 can be used as a massage and/or relaxation device for treating sore muscles and the like. For instance, the therapeutic device 100 can be first heated or cooled, and then a concave work surface 132, 134 thereof can be rolled along the spine to treat sore back muscles. Alternatively, the convex working surface 130 can be used, in conjunction with heat or cold, to work any other body region, muscle, or group of muscles.

Having thus described the preferred embodiments, the invention is now claimed to be:

1. A therapeutic device for treating foot pathologies, the device comprising a generally-cylindrical body having a first end section, a convexly curved center section, a first intermediate section extending axially between the first end section and the center section, a second end section, and a second intermediate section extending axially between the second end section and the center section, the center section defining a spherical working surface, the first intermediate section cooperating with the first end section and the spherical working surface of the center section to define a first hourglass-shaped working surface, and the second intermediate section cooperating with the second end section and the spherical working surface of the center section to define a second hourglass-shaped working surface that is shaped the same as but dimensioned differently from said first hourglass-shaped working surface, wherein:

said first end section, said section second end section and said center section each are adapted to contact and rollably support said device on a support surface;

said first intermediate section has a first diameter and a first length and said second intermediate section has a second diameter greater than said first diameter and a second length greater than said first length; and, the spherical working surface of the center section is adapted to contact a center region of a plantar fascia of an associated foot, the first hourglass-shaped working surface is adapted to contact intermediate regions of a plantar fascia of an associated foot, and the second hourglass-shaped working surface is adapted to contact side regions of a plantar fascia of an associated foot.

* * * * *